United States Patent [19]

Moore, Jr.

[11] 4,218,371
[45] Aug. 19, 1980

[54] PROCESS FOR PREPARING 2,2'-AZOBIS(2,4-DIMETHYL-4-METHOXYPENTANENITRILE)

[75] Inventor: Earl P. Moore, Jr., Hockessin, Del.

[73] Assignee: E. I. Du Pont de Nemours and Company, Wilmington, Del.

[21] Appl. No.: 944,571

[22] Filed: Sep. 25, 1978

Related U.S. Application Data

[63] Continuation-in-part of Ser. No. 851,389, Nov. 14, 1977, Pat. No. 4,132,729.

[51] Int. Cl.$^2$ .................... C07C 107/02; C08F 2/04; C08F 2/24; C08F 2/28
[52] U.S. Cl. .................................. 260/192; 526/220
[58] Field of Search ........................................ 260/192

[56] References Cited

U.S. PATENT DOCUMENTS

| | | | |
|---|---|---|---|
| 2,711,405 | 6/1955 | Anderson | 260/192 |
| 3,783,148 | 1/1974 | Fuchs | 260/192 |
| 3,937,696 | 2/1976 | Knowles et al. | 260/192 |
| 3,987,025 | 10/1976 | Moore | 260/192 |
| 4,028,345 | 6/1977 | Moore | 260/192 |
| 4,039,527 | 8/1977 | Nagaoka et al. | 260/192 |
| 4,051,124 | 9/1977 | Moore | 260/192 |
| 4,061,590 | 12/1977 | Moore | 260/192 |

*Primary Examiner*—Floyd D. Higel

[57] ABSTRACT

A process for the preparation of 2,2'-azobis(2,4-dimethyl-4-methoxypentanenitrile) in improved yields with improved filtering characteristics, said process comprising reacting 2-amino-2,4-dimethyl-4-methoxypentanenitrile with a metal hypochlorite in the presence of water, a quaternary ammonium surface active compound and ionic bromide wherein the equivalent ratio of ionic bromide to surface active compound is 0.4:1–4:1 at a temperature of about −10° C. to about 30° C., and recovering 2,2'-azobis(2,4-dimethyl-4-methoxypentanenitrile) from the reaction mixture.

22 Claims, No Drawings

PROCESS FOR PREPARING 2,2'-AZOBIS(2,4-DIMETHYL-4-METHOXYPENTANENITRILE)

CROSS REFERENCE TO RELATED APPLICATION

This application is a continuation-in-part of copending application Ser. No. 851,389, filed Nov. 14, 1977, and now U.S. Pat. No. 4,132,729.

DESCRIPTION

1. Technical Field

This invention relates to an improved process for the preparation of 2,2'-azobis(2,4-dimethyl-4-methoxypentanenitrile) from 2-amino-2,4-dimethyl-4-methoxypentanenitrile, water, a metal hypochlorite and a surface active compound. More specifically, this invention relates to a process for the preparation of 2,2'-azobis(2,4-dimethyl-4-methoxypentanenitrile) in improved yield and with improved filtering characteristics by reacting an aqueous hypochlorite solution with 2-amino-2,4-dimethyl-4-methoxypentanenitrile in the presence of a surface active compound and an ionic bromide.

2. Background Art

Azonitriles are produced by a process described by Anderson in U.S. Pat. No. 2,711,405 which involves reacting the cyanohydrin of an aliphatic ketone with ammonia to form an aminonitrile and oxidatively coupling the aminonitrile to form the azo using an alkali metal or alkaline earth metal hypochlorite in aqueous medium. De Benneville in U.S. Pat. No. 2,713,576 claimed essentially the same process with the addition of alkyl hypochlorites and restriction of aminonitriles to those of acetone, methyl ethyl ketone and diethyl ketone. A process improvement which enables azonitriles to be prepared from aminonitriles of higher molecular weight ketones in good yields is reported by Fuchs in U.S. Pat. No. 3,783,148. Methanol or ethanol is employed as a reaction solvent in proportion to the amounts of aminonitrile and hypochlorite solution used such that, at the completion of the reaction, the alcohol concentration is at least 70% by volume. The alcohol maintains a homogeneous system throughout the reaction and specifically prevents separation of the intermediate, highly hydrophobic chloramines.

U.S. Pat. No. 4,028,345 discloses a process which does not involve the alcohol solvent with all its drawbacks by coupling alpha-aminonitriles in the presence of a metal hypochlorite, water and a surface active compound to form aliphatic azodinitriles.

U.S. Pat. No. 4,051,124 discloses a process for preparing 2,2'-azobis(isobutyronitrile) by coupling 2-amino-2-methylpropionitrile in the presence of a metal hypochlorite, water and a mixture of a quaternary ammonium compound and a nonionic or amphoteric surface active compound. The 2,2'-azobis(2,4-dimethyl-4-methoxypentanenitrile) produced by the aforesaid process has poor filtering characteristics and is obtained in less than desired yields.

DISCLOSURE OF THE INVENTION

Now it has been found that when 2,2'-azobis(2,4-dimethyl-4-methoxypentanenitrile) is prepared from 2-amino-2,4-dimethyl-4-methoxypentanenitrile by reaction with a metal hypochlorite in the presence of water and a surface active compound, the 2,2'-azobis(2,4-dimethyl-4-methoxypentanenitrile) is produced in higher yield and isolated by filtration from the reaction mixture much more rapidly when the surface active compound is a quaternary ammonium salt of a particular chemical structure and there is also present ionic bromide. Accordingly, the process of the present invention comprises reacting 2-amino-2,4-dimethyl-4-methoxypentanenitrile with a metal hypochlorite in an aqueous medium in the presence of a surface active quaternary ammonium salt and optionally an ionic organic or ionic inorganic bromide compound in a concentration such that the equivalent ratio of ionic bromide ($Br^-$) to surface active compound is from 0.4:1–4.0:1 at a temperature of about $-10°$ C. to about $30°$ C., said metal hypochlorite and aminonitrile being present in an equivalent ratio of from 1.4:1–2:1 of hypochlorite to aminonitrile and separating the precipitated 2,2'-azobis(2,4-dimethyl-4-methoxypentanenitrile) from the reaction mixture. This separation is rapidly done by filtration. The azodinitrile is thus prepared in a superior yield and possesses improved filterability. The reaction mixture is preferably treated with $SO_2$ and optionally a mineral acid sufficient to give a reaction mixture pH of from 2–5 before separation of the azodinitrile.

In the process of this invention, two molecules of the 2-amino-2,4-dimethyl-4-methoxypentanenitrile are coupled to form the azodinitrile of the present invention. The coupling of the two molecules is accomplished in an aqueous medium with a metal hypochlorite and a surface active compound comprising a quaternary ammonium compound and ionic bromide or a mixture of a surface active compound and an ionic organic or ionic inorganic bromide compound.

By metal hypochlorite is meant a compound of the formula $M(OCl)_x$ where M is selected from the group consisting of sodium, potassium, calcium and mixtures thereof and x is the valence of M.

The preferred hypochlorite of the present invention, for reasons of convenience and economy, is sodium hypochlorite. Sodium hypochlorite can be prepared by passing chlorine gas into an aqueous sodium hydroxide solution at about $0°$ C. or it can be purchased commercially. Other hypochlorites can be prepared analogously. Two important requirements must be met for the hypochlorite to be suitable for use in this invention:

(1) The excess base used to stabilize the hypochlorite solution may be any water soluble base, preferably sodium or potassium hydroxide, but since sodium hydroxide is normally used in the commercial preparation of sodium hypochlorite, the most preferred base is sodium hydroxide and the amount of excess base must be at least 20 g/l, preferably 20–50 g/l and most preferably 20–35 g/l based on one liter of 15% by weight metal hypochlorite. The excess base may, however, be added separately to the reaction mixture or to the hypochlorite.

(2) The metal chlorate impurity level in the hypochlorite must be no more than 0.6% by weight based on 15% by weight metal hypochlorite, preferably no more than 0.3%.

Poor yield of the azonitrile will result or an oily product will be obtained if the excess base and metal chlorate is not within the above limits. Said base and chlorate levels can be readily controlled by known manufacturing procedures.

The concentration of metal hypochlorite in the aqueous medium initially is from 5–11% by weight, preferably 5–9%. At hypochlorite concentrations below 5% product yields tend to drop off. Above about 11% hypochlorite concentration, colored product tends to form. A slurry solids content of 8% can be obtained with a 9% hypochlorite concentration. When the hypochlorite is calcium hypochlorite, the preferred concentration is reached by dilution with water. Calcium hypochlorite is available as a 100% active material. Sodium hypochlorite is commercially available as a 15% by weight aqueous solution. The equivalent ratio of metal hypochlorite to the pentanenitrile is generally from 1.4:1–2:1. Ratios below 1.4:1 will not result in the improvements of higher yield and improved filterability or will not result in product formation. However, ratios above 2:1 do result in product formation, but offer no advantage. The aforesaid ratio of 1.4:1–2:1 results in high yields. The preferred ratio of the hypochlorite to the pentanenitrile is from 1.5:1–1.8:1. The equivalent ratio referred to herein is defined as the equivalent of metal hypochlorite per mole of aminonitrile. An equivalent of metal hypochlorite is a mole of the hypochlorite divided by the valence of the metal. An equivalent of aminonitrile is the same as the molar amount of aminonitrile.

The 2-amino-2,4-dimethyl-4-methoxypentanenitrile starting material of the present invention can be obtained from commercial sources or may be prepared by methods well known in the art, for example, by the method described by Knowles in U.S. Pat. No. 3,541,132. A procedure that can be used to obtain the amino compound involves charging 4-methoxy-4-methyl-2-pentanone to a platinum-lined pressure vessel and cooling this to 5° C. and then adding 1.0% of triethylamine based on the ketone weight. Hydrogen cyanide is then introduced in portions in an amount equimolar to that of the ketone at a temperature between 5° C. and 20° C. The reaction vessel is warmed to room temperature and pressurized to 40 psig with ammonia, heated to 40° C. and held at 40° C. and 80 psig for 8 hours and finally cooled and the product is discharged from the vessel.

The 2-amino-2,4-dimethyl-4-methoxy pentanenitrile that is formed with the reaction of 4-methyl-4-methoxy-2-pentanone, ammonia and HCN according to U.S. Pat. No. 3,541,132, unlike the other aminonitriles that are thus prepared, is miscible with water and thus is prepared as a homogeneous liquid mixture containing water. One mole of the ketone reacts with one mole of hydrogen cyanide and one mole of ammonia to form one mole of aminonitrile and one mole of water. Thus, the reaction product, when the pentanenitrile is prepared, comprises a solution of water in the pentanenitrile. Due to said miscibility, the water levels normally present in said pentanenitrile cannot be easily reduced to acceptable levels. Removal of substantially all of the water present in said pentanenitrile solution can, if desired, be achieved by a process comprising treating a solution of water in 2-amino-2,4-dimethyl-4-methoxy pentanenitrile with sufficient ammonia to form an ammonia concentration in the water-ammonia composition of at least 18% by weight at from 0°–50° C. to cause an aqueous layer and a pentanenitrile layer to form and separating the pentanenitrile layer and the aqueous layer. The pentanenitrile layer can then be further purified by the removal of residual ammonia. The removal of substantially all of the water present in the pentanenitrile solution permits the easy removal of ammonia. Generally the ammonia is removed from the pentanenitrile by degassing operations, e.g., by drawing a vacuum over the pentanenitrile or by passing air or nitrogen through the pentanenitrile layer.

Water separates from the pentanenitrile when the concentration of ammonia in the aqueous ammonia solution is at least 18% by weight. Cooling of the resulting ammonia-water-pentanenitrile mixture facilitates the phase separation of water and pentanenitrile. However, cooling is not mandatory. Likewise, external addition of ammonia may not be required to attain the level of at least 18% described herein. In the preparation of the pentanenitrile by the process disclosed in U.S. Pat. No. 3,541,132 steps, e.g., cooling, can be taken to prevent the loss of unreacted ammonia after the pentanenitrile preparation is complete and is discharged from the reactor. Thus, by preventing the loss of ammonia that normally occurs when the pentanenitrile product is discharged, the external addition of ammonia may not be required or lesser amounts will have to be added. Normally, however, the aminonitrile reaction product of U.S. Pat. No. 3,541,132 is warmed in order to facilitate the venting of the residual ammonia to a level which enables the aminonitrile product to be subsequently handled without undesirable evolution of ammonia and foaming. Therefore, it is generally necessary to add ammonia to the pentanenitrile solution.

The ammonia treatment results in the formation of two phases. The aqueous phase and the pentanenitrile phase are separated generally by removing the aqueous phase from the pentanenitrile phase and then air or nitrogen is passed through the pentanenitrile phase to remove the ammonia that remains in said pentanenitrile. This removal of the ammonia after water removal can be accomplished in half the time required when the water is not removed. However, the removal of water in the aforesaid manner from the pentanenitrile is not required in the process of the present invention but is preferred.

The use of surface active compounds in the preparation of azodinitrile compounds is disclosed in U.S. Pat. Nos. 4,028,345 and 4,051,124. The disclosure in said U.S. patents is hereby incorporated by reference in the present application. While the function of the surface active compound in promoting this reaction is unknown, it may be as a "catalyst" for the reaction of base (e.g., NaOH) with intermediate formed chloramines and/or it may serve as a "solubilizer" for the chloramine and base, or it may perform some other function which enables a reaction to occur. The use of a quaternary ammonium compound and ionic bromide which may be a part of the quaternary ammonium compound or a separate ionic inorganic or ionic organic bromide compound is a critical feature of the present invention. Although the function of the ionic bromide, Br−, is not clearly understood, the reaction of Br− and hypochlorite is known to form hypobromite, which may act to more efficiently promote the formation of azodinitrile from the aminonitrile and influence the physical character of the azodinitrile such that a superior yield and filtration behavior are obtained.

The quaternary ammonium compounds of this invention, their properties and behavior are discussed by Paul Becher in "Emulsions, Theory and Practice", ACS Monograph No. 162, 1965. Although the presence of the quaternary ammonium compound of the present invention is critical, the amount may vary widely. As little as 1.25% by weight of quaternary ammonium compound based upon the weight of the pentanenitrile can be used. As much as 6.5% can be used. No advantage is realized in using more than 6.5% and a tendency to produce a product with higher color may result at levels about 6.5%. The preferred range of 2.0-4.0% by weight of quaternary ammonia compound based on the aminonitrile gives the most desirable yield and filtration properties.

The quaternary ammonium compounds of this invention are specifically tetraalkylammonium compounds. These compounds have the general formula

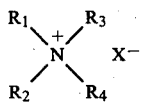

where $R_1$, $R_2$, $R_3$ and $R_4$ are alkyl groups with 1-14 carbon atoms, with at least two alkyl groups having 6-14 carbon atoms. The total number of carbon atoms in $R_1+R_2+R_3+R_4$ ranges from 16-30. The preferred total number of carbon atoms is 18-26 and the preferred quaternary ammonium compounds are those with two alkyl groups of 7-12 carbon atoms and two methyl groups. X is chloride, bromide, hydroxide, acetate, formate or any other anionic group which does not deleteriously affect the performance of the quaternary ammonium cation. The preferred groups are chloride, bromide, hydroxide, acetate and formate.

Representative examples of tetraalkylammonium surface active compounds of the present invention include:
Dioctyldimethylammonium chloride
Didodecyldimethylammonium chloride
Hexyltetradecyldimethylammonium bromide
Dihexyldiethylammonium acetate
Trioctylmethylammonium bromide.

For economic and commercial availability reasons the tetraalkylammonium chloride compounds are preferred. Most preferred is dioctyldimethylammonium chloride.

The sources of bromide ion ($Br^-$) in this invention may be either inorganic or organic. Thus, any water soluble salt of bromine may be used. These include NaBr, KBr, $CaBr_2$, LiBr, $MgBr_2$ and other inorganic bromides as well as organic amine hydrobromides such as trimethylamine hydrobromide and pyridine hydrobromide and quaternary ammonium bromides such as tetraethylammonium bromide and various surface active compounds containing the bromide ion that qualify as surface active compounds. Thus, a quaternary ammonium compound which is used in the preparation of an azodinitrile can also serve as a total or partial source of bromide ion. That is, a quaternary ammonium bromide can be employed. The process of the present invention involves the presence of certain ratios of ionic bromide to surfactant. The level of bromide used in conjunction with the surfactant to promote the formation of the azodinitrile compound from aminonitrile is best expressed in terms of an equivalent ratio of bromide ion to quaternary ammonium compound. An equivalent ratio can be as low as 0.4:1 and as high as 4.0:1 in order to obtain the benefits of the process of this invention. Use of lower or higher ratios tends to produce course or yellow or slow filtering azodinitriles. A more preferable equivalent ratio of bromide ion to quaternary ammonium compound is 0.6:1-2.5:1. A most preferred ratio is 1.7:1.

The atmospheric pressure system is entirely aqueous, requiring no organic solvent to be present as a promoter or cosolvent with water in the preferred system. The quaternary ammonium surface active compound and bromide are mixed with the water as is the sodium hypochlorite or other metal hypochlorite and the aminonitrile is added with sufficient cooling to handle the heat load. The manner in which the sodium hypochlorite and aminonitrile are combined is a matter of choice. The reactants can be added in separate streams to a body of water containing the surface active compound and bromide or the aminonitrile can be added to an aqueous metal hypochlorite solution containing the surfactant and bromide. In the present preferred system much higher azo solids slurries are possible than with the Fuchs process, enabling higher throughput with time and labor savings providing economic benefits. Thus, while product slurries with about 3% solids are obtained with the Fuchs process, the solids content of slurries of the present process is limited only by the upper useful limit of the hypochlorite concentration, which for this system, is about 11%.

The preferred temperature of the present process is $-10°$-$0°$ C., but temperature may vary beyond our preferred temperature range in the process of the present invention. Desirable yields can be obtained at temperatures as high as 30° C. and as low as $-10°$ C. The process of the present invention can be conducted at temperatures below $-10°$ C. but at such lower temperatures, the danger of freezing of the aqueous mixture becomes greater and reaction times become larger. The use of antifreeze compounds may permit operation of the present process at temperatures lower than $-10°$ C. without freezing. The process of the present invention can also be carried out at temperatures above 30° C. but at higher temperatures the risk of side reactions, azo decomposition and lower product yields, become a serious consideration. Thus, the process of the present invention may be conducted at a temperature that is above the freezing point of the reaction mixture and below the decomposition temperature of the azodinitrile compound.

The time required to complete the reaction of the present invention requires about 30 minutes at the preferred temperature.

Following completion of the reaction, the reaction mixture is a slurry of solid product partially in the form of very fine particles. It is desirable to treat the slurry with a chemical reducing agent in order to produce a product with good color and to eliminate odor causing impurities. Sulfur dioxide ($SO_2$) under acid conditions does an excellent job of effecting this, as described in U.S. Pat. No. 4,028,345. In the present invention the use of $SO_2$ at a slurry pH of 2.0-5.0, adjusted with a mineral acid, is preferred at 0°-10° C. with a treatment time of about 30 minutes. The pH can then be increased to greater than 7.0 to prevent equipment corrosion during filtration. A suitable amount of $SO_2$ for this invention is about 0.12 lb per lb of aminonitrile reacted with hypochlorite.

The filter time is the time required to remove the liquid in the reaction product slurry leaving a wet cake of product. The wash time is the time required to wash out with water impurities in the wet cake and to remove said water. In the examples that follow, the pentanenitrile was treated to remove water by the aforesaid preferred process.

COMPARATIVE EXAMPLE 1

Forty-five grams of 2-amino-2,4-dimethyl-4-methoxypentanenitrile (AN) of 86.2% purity were added to a stirred mixture of 308 g 9% sodium hypochlorite solution containing 0.1% by weight of sodium chlorate and 20 g of NaOH per liter of hypochlorite and 0.9 g dioctyldimethylammonium chloride cooled at −5° C. The equivalent ratio of NaOCl-to-aminonitrile was 1.5:1, the NaOCl concentration was 9% and the amount of surfactant was 2.0% of the aminonitrile weight. After about 35 g of AN had been added, a pale yellow sticky solid formed. The reaction mixture was stirred for 30 minutes at −5° C. and treated with 5.0 g $SO_2$ at a pH of 3.0 obtained by HCl addition. The soft solid product was not filtered because of the nature of the product.

BEST MODE

EXAMPLE 1

(A surfactant of the invention with bromide ion)

The preparation of Comparative Example 1 was repeated except this time 0.52 g sodium bromide was added to the hypochlorite-surfactant mixture to give a NaBr:surfactant equivalent ratio of 1.7:1. Following completion of the reaction period and $SO_2$ treatment, the reaction mixture was neutralized to pH 11.0 with NaOH and filtered. Filtration was conducted through 11.0 cm Whatman #41 paper on a Büchner funnel under 5 in. Hg vacuum. The cake was washed with a volume of water equal to twice the volume of the reaction mixture. Times for filtration and washing were recorded as 50 seconds and 2 minutes, respectively. The cake was then pressed under full vacuum until no more water was removed and dried at 40° C. under an air flow. The dry product weighed 37.5 g, a 97.9% yield.

COMPARATIVE EXAMPLE 2

(Using bromide ion and a surfactant with one alkyl group of 16 carbon atoms outside the scope of the invention)

Forty-five grams of 2-amino-2,4-dimethyl-4-methoxypentanenitrile (AN) of 85.9% purity were added over a period of 30 minutes to a stirred mixture of 307 g 9% sodium hypochlorite solution and 2.25 g hexadecyltrimethylammonium chloride and 0.72 g sodium bromide cooled at −5° C. The equivalent ratio of NaOCl-to-aminonitrile was 1.5, the NaOCl concentration was 9%, the amount of surfactant was 5% of the aminonitrile weight and the equivalent ratio of NaBr-to-surfactant was 1.0. After the reaction mixture was stirred for 60 minutes at −5° C. and treated with $SO_2$ at pH 2.0, it was neutralized and filtered and dried as described in Example 1.

Filter Time: 2 minutes, 30 seconds
Wash Time: 3 minutes, 30 seconds.

This total time was more than twice that in Example 2.

The yield of dry product was 33.7 g, 88.3%, almost 10% lower than in Example 1.

EXAMPLES 2–5

Following the procedure of Example 1, 2,2'-azobis(2,4-dimethyl-4-methoxypentanenitrile) is prepared by substituting the same amount of the following quaternary ammonium compounds for dioctyldimethylammonium chloride and using an amount of $Br^-$ from NaBr to give the equivalent ratios denoted:

| Example | Quaternary Compound | Equiv. Ratio $Br^-$:Quaternary Compound |
|---|---|---|
| 2 | Didecyldimethylammonium chloride | 2.0 |
| 3 | Hexyltetradecyldimethylammonium chloride | 3.5 |
| 4 | Dihexyldiethylammonium acetate | 0.75 |
| 5 | Trioctylmethylammonium bromide | 1.0 (No $Br^-$ added) |

| Example | Approx. Yield Azonitrile (%) | Filter Time | Wash Time |
|---|---|---|---|
| 2 | 97.0 | 52 sec. | 2 min., 15 sec. |
| 3 | 96.0 | 57 sec. | 2 min., 25 sec. |
| 4 | 95.0 | 1 min., 15 sec. | 2 min. |
| 5 | 93.0 | 1 min., 25 sec. | 2 min. 30 sec. |

EXAMPLES 6–9

The azonitrile, 2,2'-azobis(2,4-dimethyl-4-methoxypentanenitrile), is prepared in high yield according to the procedure of Example 1, except that the following percentages of dioctyldimethylammonium chloride surfactant were used with the following bromide compounds to give an equivalent ratio of bromide-to-surfactant of 2.0.

| Example | Surfactant Conc. as % of Aminonitrile Wt | Bromide Compounds |
|---|---|---|
| 6 | 1.25 | KBr |
| 7 | 2.0 | LiBr |
| 8 | 4.5 | $CaBr_2$ |
| 9 | 6.25 | $(CH_3)_4N^+Br^-$ |

| Example | Approx. Yield Azonitrile (%) | Filter Time | Wash Time |
|---|---|---|---|
| 6 | 95.5 | 1 min. | 2 min., 10 sec. |
| 7 | 97.5 | 1 min., 5 sec. | 1 min., 55 sec. |
| 8 | 96.5 | 1 min., 10 sec. | 2 min., 5 sec. |
| 9 | 96.0 | 55 sec. | 2 min. |

EXAMPLE 10

(Treated Pentanenitrile)

Forty-five grams of 2-amino-2,4-dimethyl-4-methoxy pentanenitrile of 87.0% purity after treatment with $NH_3$ at 28° C., separated from the resulting layer of 30% $NH_3$ in water and purged of remaining $NH_3$, were added in 30 minutes to a stirred solution of 311 g 9% NaOCl, 0.9 g dioctyldimethylammonium chloride and 0.52 g NaBr cooled at −5° C. The mixture was stirred for 30 minutes at −5° C. to complete the reaction and then treated with 5.0 g $SO_2$ and sufficient acid (HCl) to give a pH of 3.0 and stirred for 15 minutes at 10° C. The pH was finally adjusted to 11.0.

The product slurry was filtered through 11.0 cm Whatman 41 paper and the cake was washed with 800 ml water under 4 inches Hg vacuum. Filter time was 1 minute, 10 seconds, wash time was 2 minutes, 50 seconds.

The dried azonitrile weighed 37.4 g, a 96.8% yield, and had an APHA color (2% in dimethyl formamide) of 10.

INDUSTRIAL APPLICABILITY

The azodinitrile compound produced by the process of this invention can be used as a polymerization initiator in emulsion dispersion and solution systems. Polymerizations involving vinyl chloride, methyl methacrylate and butadiene-styrene are merely examples of such systems in industry that would benefit from the use of such initiators.

What is claimed is:

1. A process for the preparation of 2,2'-azobis(2,4-dimethyl-4-methoxypentanenitrile) comprising:
   (a) reacting at a temperature of from $-10°$ C. to $30°$ C.;
       (i) 2-amino-2,4-dimethyl-4-methoxypentanenitrile;
       (ii) a 5 to 11% by weight aqueous metal hypochloride solution containing 20–50 g of excess base per liter and a maximum metal chlorate content of 0.6% by weight based on a 15% by weight aqueous metal hypochlorite solution;
       (iii) an ionic organic or inorganic bromide compound; and
       (iv) at least 1.25% by weight based on the pentanenitrile of a quaternary ammonium compound of the formula $$\begin{array}{c} R_1 \diagdown \diagup R_3 \\ N^+ \quad X^- \\ R_2 \diagup \diagdown R_4 \end{array}$$

where $R_1$, $R_2$, $R_3$ and $R_4$ are each alkyl groups of 1–14 carbon atoms and where at least two alkyl groups of 6–14 carbon atoms are present with a total number of carbon atoms of 16–30 and X is bromide, chloride, hydroxide, acetate, formate or any other anionic group which does not deleteriously affect the performance of the quaternary ammonium cation, provided that if X is bromide, component (iii) need not be present; the equivalent ratio of (ii) to (i) being from 1.4:1 to 2:1 and of bromide ion to (iv) being from 0.4:1 to 4.0:1, and
   (b) recovering the 2,2'-azobis(2,4-dimethyl-4-methoxypentanenitrile) produced.

2. The process of claim 1 wherein the amount of the quaternary ammonium compound is 1.25–6.5% by weight of the pentanenitrile.

3. The process of claim 1 wherein X is bromide.

4. The process of claim 1 wherein $R_1$, $R_2$, $R_3$ and $R_4$ are two alkyl groups of 7–12 carbon atoms and two methyl groups.

5. The process of claim 1 wherein the amount of the quaternary ammonium compound is from 2–4%.

6. The process of claim 1 wherein the equivalent ratio of bromide to quaternary ammonium compound is 0.6:1–2.5:1.

7. The process of claim 1 wherein the bromide compound is sodium bromide.

8. The process of claim 1 wherein X is chloride, bromide, hydroxide, acetate, or formate.

9. The process of claim 1 wherein the metal hypochlorite solution contains 20–35 g excess base per liter.

10. The process of claim 9 wherein the amount of the quaternary ammonium compound is 1.25–6.5%.

11. The process of claim 9 wherein X is bromide.

12. The process of claim 9 wherein $R_1$, $R_2$, $R_3$ and $R_4$ are two alkyl groups of 7–12 carbon atoms and two methyl groups.

13. The process of claim 9 wherein the amount of the quaternary ammonium compound is 2–4%.

14. The process of claim 9 wherein the equivalent ratio of bromide to quaternary ammonium compound is 0.6:1–2.5:1.

15. The process of claim 1 wherein the reaction is conducted in the presence of the quaternary ammonium compound and the ionic organic or ionic inorganic bromide compound.

16. The process of claim 15 wherein the quaternary ammonium compound is dioctyldimethylammonium chloride.

17. The process of claim 15 wherein X is chloride, bromide, hydroxide or formate.

18. The process of claim 15 wherein the amount of quaternary ammonium compound is 1.25–6.5% by weight of the pentanenitrile.

19. The process of claim 15 wherein X is chloride.

20. The process of claim 15 wherein the bromide compound is sodium bromide.

21. The process of claim 15 wherein the equivalent ratio of bromide to quaternary ammonium compound is 0.6:1–2.5:1.

22. The process of claim 15 wherein $R_1$, $R_2$, $R_3$ and $R_4$ are two alkyl groups of 17–12 carbon atoms and two methyl groups.

* * * * *

UNITED STATES PATENT OFFICE
CERTIFICATE OF CORRECTION

PATENT NO. : 4,218,371
DATED : August 19, 1980
INVENTOR(S) : Earl P. Moore, Jr.

It is certified that error appears in the above-identified patent and that said Letters Patent are hereby corrected as shown below:

Column 10, line 49, Claim 22, "17-12" should read --7-12--.

Signed and Sealed this

Fourteenth Day of April 1981

[SEAL]

Attest:

RENE D. TEGTMEYER

Attesting Officer     Acting Commissioner of Patents and Trademarks